(12) United States Patent
Ulm

(10) Patent No.: US 7,603,723 B2
(45) Date of Patent: Oct. 20, 2009

(54) THERAPEUTIC EYE MASK

(76) Inventor: Alpha Carolyn Ulm, 2818 Woodley Rd., Montgomery, AL (US) 36111

( * ) Notice: Subject to any disclaimer, the term of this patent is extended or adjusted under 35 U.S.C. 154(b) by 348 days.

(21) Appl. No.: 11/433,116

(22) Filed: May 12, 2006

(65) Prior Publication Data

US 2007/0272246 A1  Nov. 29, 2007

(51) Int. Cl.
*A61F 9/00* (2006.01)
(52) U.S. Cl. ............................. 2/15; 604/290
(58) Field of Classification Search .................. 2/9, 2/10, 12, 15, 173; 128/206.19, 858; 604/294, 604/304, 289, 290; 602/74
See application file for complete search history.

(56) References Cited

U.S. PATENT DOCUMENTS

| 1,275,127 | A | * | 8/1918 | Campbell | 2/15 |
| 2,543,104 | A | * | 2/1951 | Golding | 602/74 |
| 4,019,516 | A | * | 4/1977 | D'Auria | 604/308 |
| 4,709,695 | A | | 12/1987 | Kohn et al. | |
| 5,425,380 | A | * | 6/1995 | Hudson et al. | 128/858 |
| D365,589 | S | | 12/1995 | Whitley et al. | |
| 5,700,238 | A | * | 12/1997 | Hyson | 602/74 |
| 5,740,550 | A | | 4/1998 | Yavitz | |
| 5,927,280 | A | * | 7/1999 | Miyake | 128/857 |
| 5,954,055 | A | * | 9/1999 | Miyake | 128/857 |
| 5,980,497 | A | | 11/1999 | Yavitz | |
| 6,098,628 | A | | 8/2000 | Funk | |
| 6,641,264 | B1 | | 11/2003 | Schwebel | |

\* cited by examiner

*Primary Examiner*—Katherine Moran
(74) *Attorney, Agent, or Firm*—C. Brandon Browning; Maynard, Cooper & Gale, PC

(57) ABSTRACT

A mask includes a flexible backing and an expandable membrane. The flexible backing is configured to overlay the eyes and nose of a wearer. The expandable membrane is coupled to the backing. The expandable membrane fills the non planar surfaces of the face when the backing exerts a pressure onto the membrane.

20 Claims, 4 Drawing Sheets

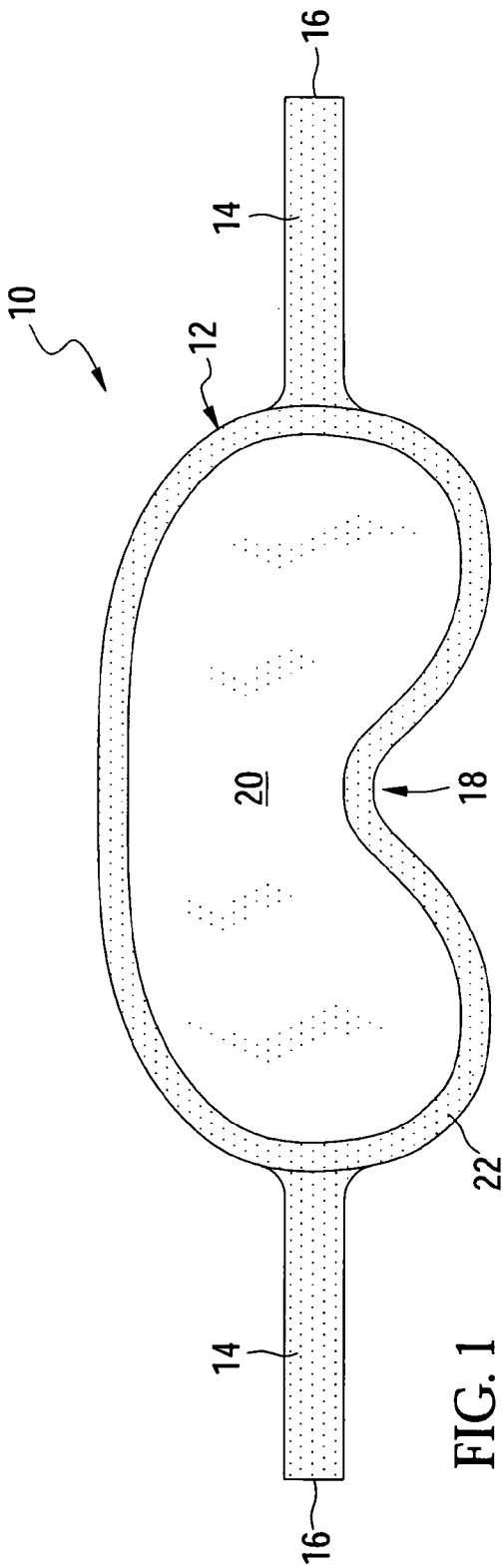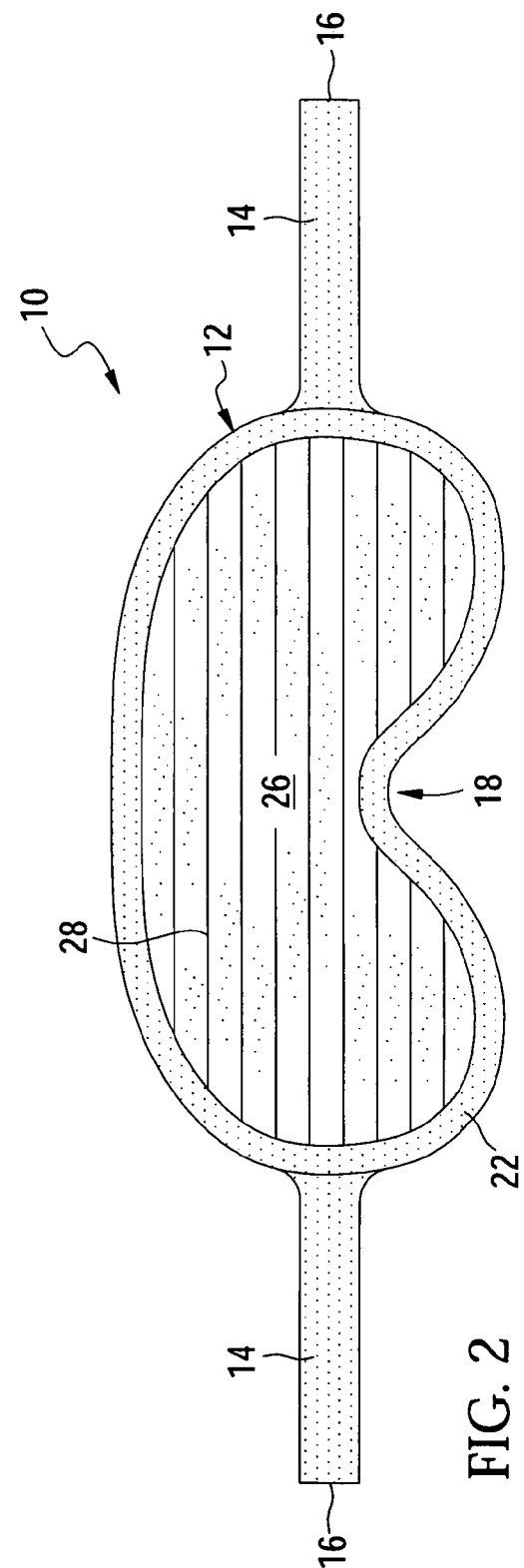

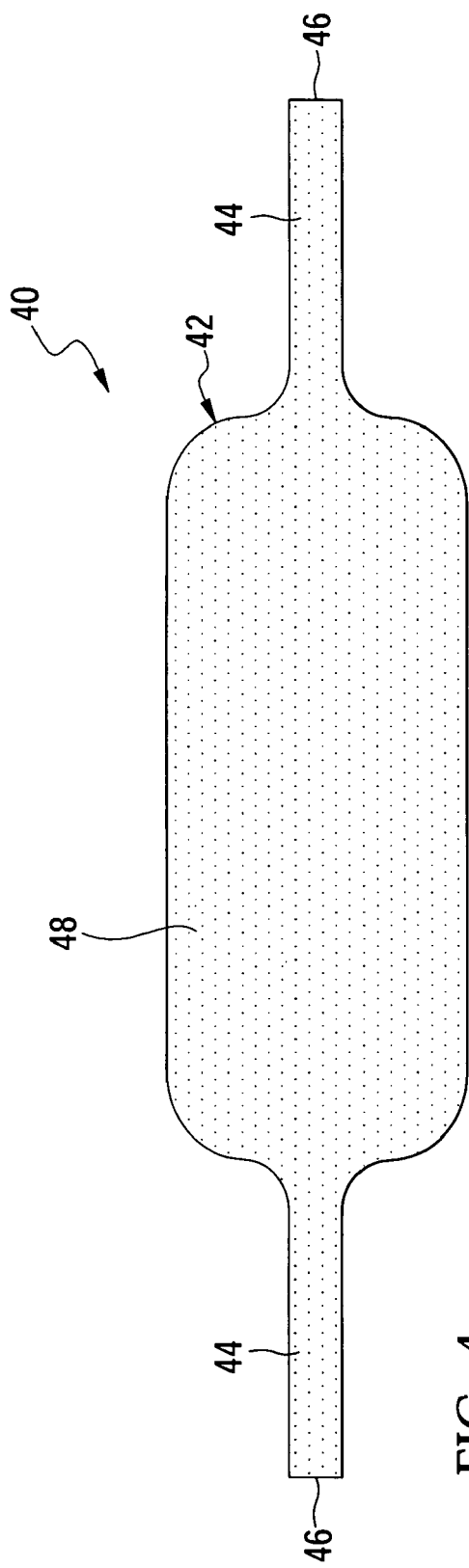
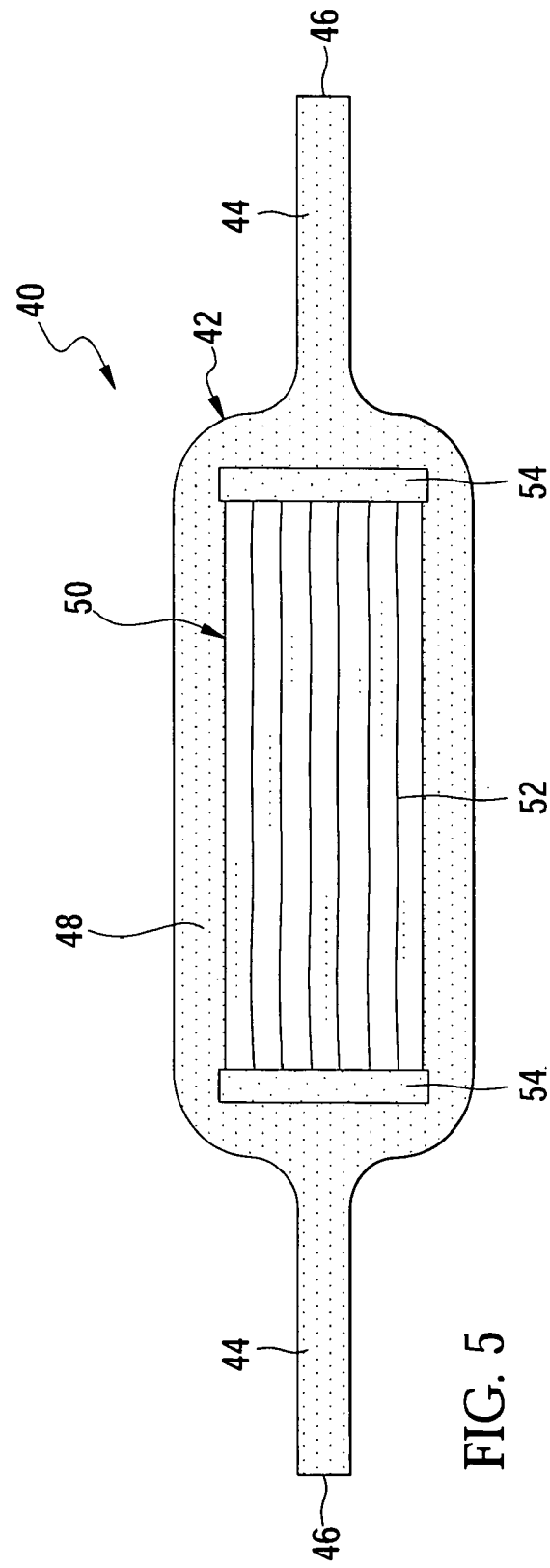
FIG. 4
FIG. 5

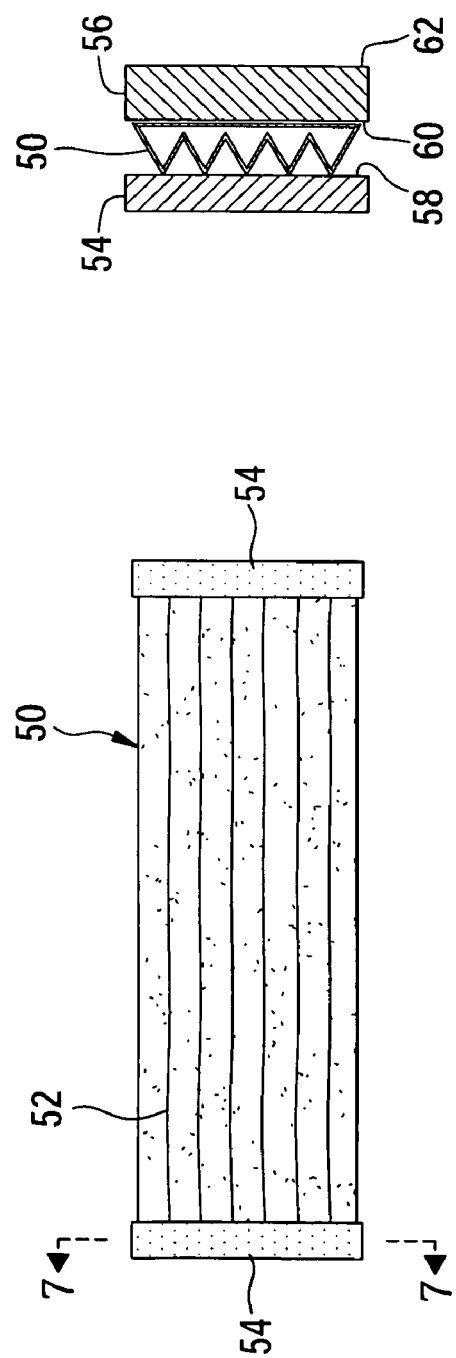
FIG. 6
FIG. 7
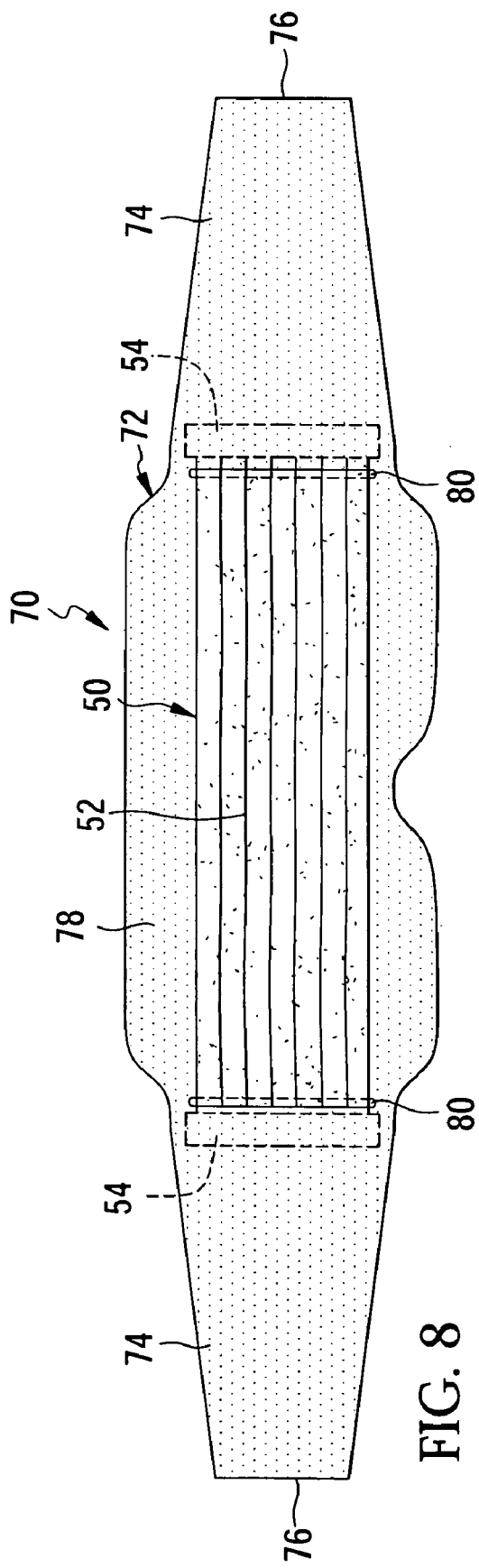
FIG. 8

THERAPEUTIC EYE MASK

FIELD OF THE INVENTION

The present invention relates generally to a therapeutic eye mask. More specifically, the invention relates to a mask having a disposable, sterile, pliable liner. The mask may be used in conjunction with eye drops and/or eye ointment, or can be used alone as a relaxation therapy.

BACKGROUND OF THE INVENTION

When eyes are dried by heat, cold or dry air, the moisture in the membranes of the eyes may evaporate. This results in the person having uncomfortably dry eyes. Maintaining moisture in the eyes is particularly difficult as people age or for individuals who suffer from certain eye disorders. Additionally, a high level of moisture in the membranes of the eyes is advantageous following certain types of eye surgeries.

In addition to dryness, eyes also are susceptible to dirt, bacteria, and other particles that may become lodged in the eye. Dirt and bacteria are especially problematic following certain eye surgeries. They are also a problem in environments where the air is recirculated, as for example, in airplanes.

One possible solution is standard goggles. Goggles may be secured over the eyes by a strap that wraps around the wearer's head. Loose straps will not adequately maintain the position of the goggles. On the other hand, if the overly tight straps may be uncomfortable and leave marks on the face. Because the goggles are also bulky, goggles are also difficult to store in a purse or a pocket.

Another example of a eye mask includes a clear, hard plastic center with a porous flap extending outwardly from the hard plastic center. The flap includes an adhesive applied to one surface to permit adherence of the flap to the face of a wearer surrounding one of the wearer's eyes. Due to the porous, vapor permeable nature of the flap, moisture, e.g., water vapor, can still escape from the region surrounding the wearer's eye, and bacteria has access to the eye. The adhesive may leave marks in the face and may not effectively secure the eye mask to the face.

SUMMARY OF THE INVENTION

A mask comprises a flexible backing configured to overlay the eyes and nose of a wearer; and an expandable membrane coupled to the backing; the expandable membrane fills the non planar surfaces of the face when the backing exerts a pressure onto the membrane.

BRIEF DESCRIPTION OF THE DRAWINGS

FIG. 1 is a front view of an embodiment of an eye mask.

FIG. 2 is a back view of the eye mask of FIG. 1.

FIG. 4 is a front view of another embodiment of an eye mask.

FIG. 5 is a back view of the eye mask of FIG. 4.

FIG. 6 is a view of a portion of the eye mask of FIG. 4.

FIG. 7 is a cutaway view of a portion of the eye mask of FIG. 6.

FIG. 8 is a back view of another embodiment of an eye mask.

DETAILED DESCRIPTION OF THE DRAWINGS

Figure 3:
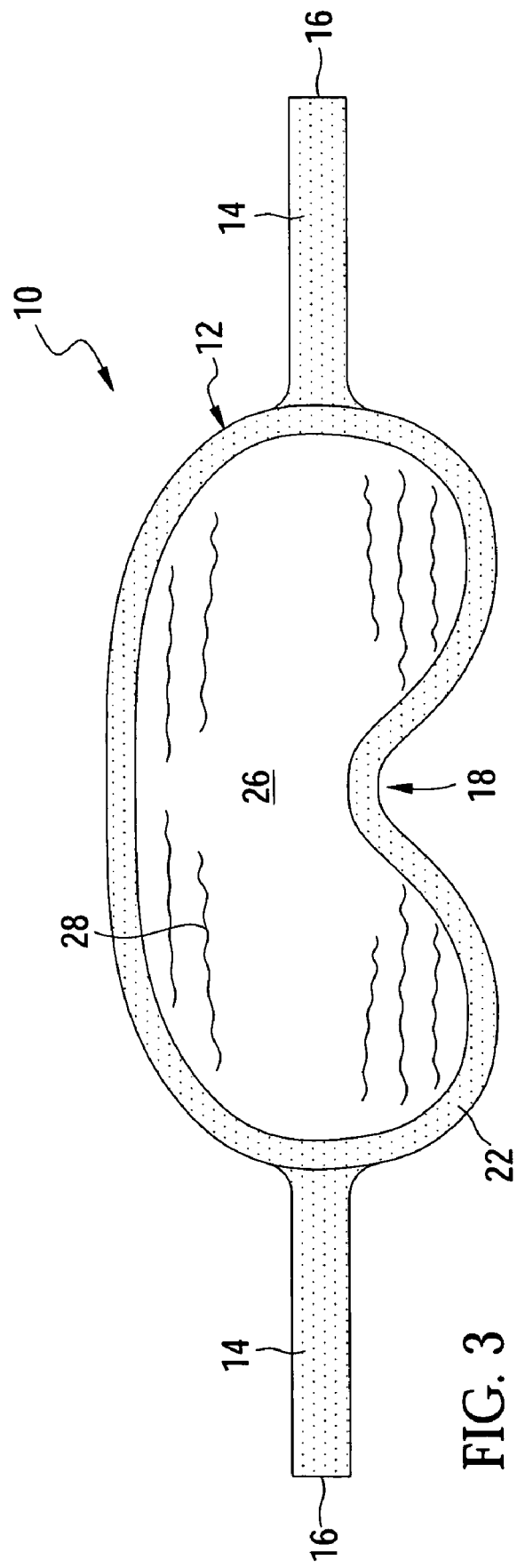
FIG. 3 is a back view of the eye mask of FIG. 1 having a partially expanded membrane.

Turning now to the drawing figures, FIG. 1 is a front view of an embodiment of an eye mask 10. The mask 10 includes an eye cover 12 and straps 14. The straps 14 terminate in strap ends 16. The eye cover 12 includes a nose bridge 18, backing 20 and a seam portion 22. The seam portion 22 attaches the straps 14 to the backing 20 on the front side of the mask 10.

When the mask 10 is placed on a wearer, the wearer's nose rests in the nose bridge 18, the backing 20 lays across the eyes of the wearer and the straps 14 are wrapped around the wearer's head. The ends 16 of the straps 14 are attached to one another through, for example, Velcro attached to the ends 16. Other connecting means, such as rings, may be used. The connecting means are meant to hold the mask in place against the wearer's face. The mask should be held in place such that the mask will maintain a slight force against the eyes if the wearer is upright or laying on their side. In another embodiment, a mask may not have straps, and only use the force of gravity to hold the mask against the wearer's face. In such an embodiment, the wearer's head would need to be under the mask, such as when the wearer is laying on her back or tilting her head backward.

The backing 20 is sized to extend over the eyes, the eye sockets, and the bridge of the nose between the eyes. The backing 20 may be made of a flexible material. In one embodiment, the material may be a paper fabric. The seam portion 22 overlaps the backing 20 and the straps 14 and may be a paper seam binding material which may also be flexible. The flexible material in the seam portion 22, the backing 20 and the straps 14 may generally conform to the non-planar surfaces of the eye sockets and surrounding face of the wearer.

Turning now to FIG. 2, FIG. 2 is a back view of the eye mask 10 of FIG. 1. The mask 10 includes many of the same elements as the mask 10 in FIG. 1. The same reference numbers are used to describe the same elements in FIG. 2. The back view of FIG. 2 also includes an expandable membrane 26. The expandable membrane 26 includes bunched creases 28 extending across the eye cover 12. The bunched creases 28 in the membrane 26 allow the membrane to conform to the contours of the face. In another embodiment, the membrane may be partially filled with a fluid. As the mask 10 is filled, the bunched creases 28 are uncreased. When the membrane 26 is partially filled, the membrane 26 is conformable to the surface on which the mask 10 is placed.

The seam portion 22 extends over the membrane 26. The seam portion 22 then extends over the backing 20 the straps 14 and the membrane 26. The seam portion 22 is folded over the edges of the backing 20 and the membrane 26 and stitched through so that the seam portion 22 encloses the backing 20 and the membrane 26. The membrane 26 may be fully enclosed such that any fluid inside the membrane 26 is sealed within the membrane 26. Such a configuration fixes the amount of fluid within the membrane 26. The straps 14 may be inset in the seam portion 22 so that when the seam portion 22 is stitched, the straps 14 are fixedly attached to the eye cover 12.

Turning now to FIG. 3, FIG. 3 is a back view of the eye mask 10 of FIG. 1 having a membrane 26 conformed to a non planar surface. The eye mask 10 of FIG. 3 is the same view as FIG. 2. In one embodiment, the eye mask 10 in FIG. 3 includes a membrane filled with fluid such that the membrane 26 remains pliant and may conform to a non planar surface, such as the surface around the eye sockets and nose. The fluid within the membrane 26 may flow across the membrane 26 and settle in the interstices formed between the backing 20 and the non planar surfaces of the face.

When a wearer places the mask 10 on the face, the backing 20 and the straps 14 are wrapped around the wearer's head. These surfaces generally contour to the most extended surfaces of the head circumferentially around the wearer's head. Under the backing 20, the membrane 26 is compressed against the face of the wearer extending into the interstices between the backing 20 and the face. The pressure in the membrane 26 created by the tension in the straps 14 and backing 20 pressing on the membrane 26 forces the membrane 26 to flow to the spaces in the eye sockets. By adjusting the tension in the straps 14 and backing 20, the amount of pressure in the membrane 26 may be increased or decreased. By increasing or decreasing the amount of fluid in the membrane 26 the amount of pressure at a given tension in the straps 14 and backing 20 may also be adjusted. By adjusting the amount of fluid, different facial geometries may be fitted. For example, a wearer having deep eye sockets may need additional fluid within the membrane 26 to fully fill the interstices between the backing 20 and the face.

When the mask 10 is properly placed on the face, the membrane 26 seals the eye sockets such that drops placed in the eye will not roll out of the eye. The gentle pressure provided by the membrane 26 minimizes any pain from masks which seal with higher pressures or adhesives which may pull on the skin when removed. The mask 10 is meant to be disposable so that no bacteria or dirt builds up on the membrane 26. In another embodiment, as discussed below with reference to FIGS. 4-7, a disposable membrane is implemented with a mask that may be reused.

Turning now to FIG. 4, FIG. 4 is a front view of another embodiment of an eye mask 40. The mask 40 includes an eye cover 42 and straps 44. The straps 44 terminate in strap ends 46. The eye cover 42 includes backing 48 which extends between the straps 44. In this embodiment, the mask 40 may be made of a flexible material that is not meant to be disposable, such as felt or leather.

When the mask 40 is placed on a wearer, the wearer's nose rests under the backing 48. The backing 48 lays across the eyes of the wearer and the straps 44 are wrapped around the wearer's head. The ends 46 of the straps 44 are attached to one another through, for example, Velcro attached to the ends 46. Other connecting means, such as rings, may be used. The connecting means are meant to hold the mask in place against the wearer's face. The mask should be held in place such that the mask will maintain a slight force against the eyes if the wearer is upright or laying on their side. Similar to an alternative embodiment of FIG. 1, a mask may not have straps, and only use the force of gravity to hold the mask against the wearer's face. In such an embodiment, the wearer's head would need to be under the mask, such as when the wearer is laying on her back or tilting her head backward.

The backing 48 is sized to extend over the eyes, the eye sockets, and the upper parts of the nose between the eyes. The backing 48 may be made of a flexible material. The flexible material of the backing 48 and the straps 44 may generally conform to the non-planar surfaces of the eye sockets and surrounding face of the wearer. The straps 44 are fixedly attached to the eye cover 42.

Turning now to FIG. 5, FIG. 5 is a back view of the eye mask of FIG. 4. The mask 40 includes many of the same elements as the mask 40 in FIG. 4. The same reference numbers are used to describe the same elements in FIG. 4. The back view of FIG. 5 also includes an expandable membrane 50. The expandable membrane 50 includes bunched creases 52 extending across the eye cover 42. A seam 54, such as an adhesive at the ends of the expandable membrane 50 seal the membrane 50 at the ends. The bunched creases 52 in the membrane 50 allow the membrane 50 to conform to the head of the wearer. Similar to the embodiments discussed above, the membrane 50 may also be filled with fluid. As the mask 40 is filled, the bunched creases 52 are filled. When the membrane 26 is partially filled, the membrane 26 is conformable to the surface on which the mask 40 is placed.

The adhesive 54 extends over the ends of the membrane 50. The adhesive 54 is then placed on the backing 50. The adhesive 54 is folded over the edges of the membrane 50 and encloses the membrane 50. The membrane 50 may be fully enclosed by the adhesive 54 such that fluid inside the membrane 50 is sealed within the membrane 50. Such a configuration fixes the amount of fluid within the membrane 50.

Turning now to FIG. 6, FIG. 6 is a view of a portion of the eye mask of FIG. 4. The membrane 50 is detachably removable from the backing 48 of the eye mask 40. The membrane 50 remains pliant and may conform to a non planar surface, such as the surface around the eye sockets and nose. The fluid within the membrane 50 may flow across the membrane 50 and settle in the interstices formed between the backing 48 and the non planar surfaces of the face.

The adhesive 54 includes portions that are folded over the ends of the membrane 50 to seal the membrane 50. As is shown in more clarity in FIG. 7, the adhesive folds over the ends of the membrane 50 and seals the membrane 50 as well as fixing the membrane 50 to the backing 48.

When a wearer places the mask 40 on the face, the backing 48 and the straps 44 are wrapped around the wearer's head. These surfaces generally contour to the most extended surfaces of the head circumferentially around the wearer's head. Under the backing 48, the membrane 50 is compressed against the face of the wearer extending into the interstices between the backing 48 and the face. The pressure in the membrane 50 created by the tension in the straps 44 and backing 48 pressing on the membrane 50 forces the membrane 50 to contour to the spaces in the eye sockets. By adjusting the tension in the straps 44 and backing 48, the amount of pressure in the membrane 50 may be increased or decreased. By increasing or decreasing the amount of fluid in the membrane 50 the amount of pressure at a given tension in the straps 44 and backing 48 may be adjusted. By adjusting the amount of fluid, different facial geometries may be fitted.

The membrane 50 may be kept in a sealed bag prior to use. This will minimize any damage that may happen to the membrane prior to use, such as contamination or ripping. The membrane 50 may be filled or unfilled with fluid within a bag. If the membrane 50 is unfilled, then the sealed bag may be small. An unfilled membrane 50 also allows for the wearer to fill the membrane 50 with an amount of fluid the wearer believes is most comfortable and effective. An unfilled membrane 50 further allows the wearer to fill the membrane 50 with a warm fluid, if the wearer finds the warm fluid to be more comfortable.

Turning now to FIG. 7, FIG. 7 is a cutaway view of a portion of the eye mask of FIG. 6. The membrane 50 is between the adhesive layers 54 and 56. The adhesive 54 includes a sticky inside surface 58. The second adhesive layer 56 has a sticky side on the inside surface 60 and the outside surface 62. The inside surfaces 58 and 60 of the adhesive layers 54 and 56 are pressed against each other to seal the open end of the membrane 50. The outside surface 62 of the adhesive layer 56 sticks to the backing 48 of the mask 40. The layers 54 and 56 may also be made from a seam binding that is folded over the end of the membrane 50. The layers 54 and 56 and the membrane 50 may be attached with stitches in this embodiment.

Turning now to FIG. 8, FIG. 8 is a back view of another embodiment of an eye mask 70. The mask 70 includes an eye cover 72 and straps 74. The straps 74 terminate in strap ends 76. The eye cover 72 includes a backing 78 which extends between the straps 74. In this embodiment, the mask 70 may be made of a flexible material that is not meant to be disposable, such as felt or leather.

The mask 70 also includes the expandable membrane 50 of FIG. 6. The expandable membrane 50 includes bunched creases 52 extending across the eye cover 42. The seam 54 at the ends of the expandable membrane 50 seal the membrane 50 at the ends. The bunched creases 52 in the membrane 50 allow the membrane 50 to conform to the head of the wearer. The membrane 50 in this embodiment is a single layer of material, such as polyurethane, cellophane, latex, or some other pliable, conformable material. The seam 54 of the membrane 50 is inserted through slots 80 in the straps 74. The membrane 50, after inserted through the slots 80, may be expanded by the wearer to increase the surface of the membrane 50 by expanding the bunched creases 52. In this manner, the membrane 50 is detachably removable from the backing 78 of the eye mask 70. Disposable membranes 50 may then be removed from the mask and replaced with fresh membranes 50. The membrane 50 remains pliant and may conform to a non planar surface, such as the surface around the eye sockets and nose.

When a wearer places the mask 70 on the face, the backing 78 and the straps 74 are wrapped around the wearer's head. These surfaces generally contour to the most extended surfaces of the head circumferentially around the wearer's head. Under the backing 78, the membrane 50 is compressed against the face of the wearer extending into the interstices between the backing 78 and the face. The pressure in the membrane 50 created by the tension in the straps 74 and backing 78 pressing on the membrane 50 forces the membrane 50 to contour to the spaces in the eye sockets. By adjusting the tension in the straps 74 and backing 78, the amount of pressure in the membrane 50 may be increased or decreased.

When the mask 70 is placed on a wearer, the wearer's nose rests under the backing 78. The backing 78 lays across the eyes of the wearer and the straps 74 are wrapped around the wearer's head. The ends 76 of the straps 74 are attached to one another through, for example, Velcro attached to the ends 76. Other connecting means, such as rings, may be used. The connecting means are meant to hold the mask in place against the wearer's face. The mask should be held in place such that the mask will maintain a slight force against the eyes if the wearer is upright or laying on their side.

While the invention has been shown in embodiments described herein, it will be obvious to those skilled in the art that the invention is not so limited but may be modified with various changes that are still within the spirit of the invention.

The following is claimed:

1. A method for retaining moisture in a user's eyes comprising,
    providing an eye mask having a left side portion arranged for covering the user's left eye, a right side portion arranged for covering the user's right eye, a nose bridge formed within a lower edge of the mask between the left side and the right side, and a disposable, plastic membrane detachably coupled to the mask, the membrane including a plurality of bunched creases, a right eye portion arranged for covering the user's right eye and a left eye portion arranged for covering the user's left eye,
    placing eye drops into the user's eyes,
    placing the eye mask on the user's face,
    contacting the right eye portion of the plastic membrane to the user's right eye socket and coupling the plurality of bunched creases to the user's skin about the user's right eye, and
    contacting the left eye portion of the plastic membrane to the user's left eye socket and coupling the plurality of bunched creases to the user's skin about the user's left eye.

2. The method according to claim 1 further comprising detachably coupling the plastic membrane to the mask by inserting the plastic membrane into two slots formed in the mask.

3. The method according to claim 1 further comprising removing the mask from the user's face, detaching the plastic membrane from the mask and detachably coupling a second plastic membrane to the mask.

4. The method according to claim 3 further comprising removing the second plastic membrane from a sealed bag prior to detachably coupling the second plastic membrane to the mask.

5. The method according to claim 1 wherein the plastic membrane is detachably coupled to the mask by inserting a first lateral edge of the membrane into a first slot formed within the mask adjacent to the right side portion and a second lateral edge of the membrane into a second slot formed within the mask adjacent to the left side portion.

6. The method according to claim 1 further comprising arranging the plurality of bunched creases to extend over the user's right eye socket and left eye socket.

7. The method according to claim 1 further comprising making the plastic membrane out of cellophane.

8. A method of retaining moisture in a user's eyes comprising,
    placing drops in the user's eyes,
    providing an eye mask including,
        a left side portion covering the user's left eye,
        a right side portion covering the user's right eye,
        a nose bridge formed within a lower edge of the mask between the left side portion and the right side portion, the nose bridge being supported about the user's nose, and
        a disposable, plastic membrane removably coupled to and between the mask and the user's eyes, the membrane including a plurality of bunched creases extending completely over the user's right eye and the user's left eye,
    contacting a right eye portion of the plastic membrane against the user's right eye socket and adhering the plurality of bunched creases about the user's right eye, and
    contacting a left eye portion of the plastic membrane against the user's left eye socket and adhering the plurality of bunched creases about the user's left eye.

9. The method according to claim 8 wherein the plastic membrane is removably coupled to the mask by inserting a first lateral edge of the membrane into a first mask pocket located adjacent to the right side portion and inserting a second lateral edge of the membrane into a second mask pocket located adjacent to the left side portion.

10. The method according to claim 9 further comprising removing the mask from the user's face, detaching the plastic membrane from the mask, removing a second plastic membrane from a bag and removably coupling the second plastic membrane to the mask.

11. The method according to claim 10 wherein the bag is a sealed bag.

12. The method according to claim 10 further comprising making the plastic membrane out of cellophane.

13. The method according to claim 8 further comprising removably coupling the plastic membrane to the mask by inserting an edge of the membrane into a mask slot.

14. A method of retaining moisture in a user's eyes comprising,
placing eye drops into the user's eyes,
providing an eye mask,
detachably coupling a disposable, first fluid impermeable membrane including a plurality of bunched creases to the eye mask,
arranging a left side portion of an eye mask over the user's left eye,
arranging a right side portion of the eye mask over the user's right eye,
resting a nose bridge formed within a lower edge of the mask between the left side portion and the right side portion on the user's nose,
arranging the plurality of bunched creases to directly contact the user's skin about the user's right eye and left eye,
removing the mask from the user's face,
detaching the first fluid impermeable membrane from the mask, and
detachably coupling a second fluid impermeable membrane including a plurality of bunched creases to the eye mask.

15. The method according to claim 14 wherein detachably coupling the first fluid impermeable membrane to the eye mask includes inserting edges of the membrane into a set of mask pockets.

16. The method according to claim 14 further comprising removing the second fluid impermeable membrane from a bag prior to coupling the second membrane to the mask.

17. The method according to claim 14 further comprising arranging at least one bunched crease of the plurality of bunched creases to extend substantially horizontally completely across and between the user's left eye and the user's right eye.

18. The method according to claim 17 wherein the plurality of bunched creases cling to the user's eye sockets.

19. The method according to claim 14 further comprising removing the mask from the user's face, detaching the a second fluid impermeable membrane from the mask and detachably coupling a second fluid impermeable membrane to the mask, the second fluid impermeable membrane being coupled to the mask at a left edge thereof to a first mask pocket in the left side portion of the mask and at a right edge thereof to a second mask pocket in the right side portion of the mask.

20. A method according to claim 19 wherein a top edge and a bottom edge of the second fluid impermeable membrane are free from direct attachment to the mask.

* * * * *